US012714403B2

(12) United States Patent
Wekselman et al.

(10) Patent No.: US 12,714,403 B2
(45) Date of Patent: Aug. 25, 2026

(54) INTRACARDIAC IMAGING USING ELECTRO-ANATOMICAL DATA TO GENERATE AUGMENTED ULTRASONIC IMAGES

(71) Applicant: BIOSENSE WEBSTER (ISRAEL) LTD., Yokneam (IL)

(72) Inventors: Guy Wekselman, Tel Aviv (IL); Lior Greenbaum, Zoran (IL); Eid Adawi, Tur'an (IL); Dan Sztejnberg, Hertzliya (IL); David Haimovich, Haifa (IL); Emuna Eliav, Pardes Hana (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 141 days.

(21) Appl. No.: 17/720,430

(22) Filed: Apr. 14, 2022

(65) Prior Publication Data

US 2023/0329678 A1 Oct. 19, 2023

(51) Int. Cl.
*A61B 8/00* (2006.01)
*A61B 5/367* (2021.01)
(Continued)

(52) U.S. Cl.
CPC ............ *A61B 8/5246* (2013.01); *A61B 5/367* (2021.01); *A61B 8/0883* (2013.01); *A61B 8/12* (2013.01);
(Continued)

(58) Field of Classification Search
CPC ....... A61B 8/5246; A61B 8/0883; A61B 8/12; A61B 8/461; A61B 2562/0223; A61B 5/287; A61B 5/6859; A61B 8/4416; A61B 8/4254; A61B 8/5261; A61B 8/483; A61B 8/463; A61M 25/0105; A61M 2025/0166
See application file for complete search history.

(56) References Cited

U.S. PATENT DOCUMENTS 5,391,199 A 2/1995 Ben-Haim
5,458,126 A * 10/1995 Cline ........................ G06T 7/11 324/309
(Continued)

FOREIGN PATENT DOCUMENTS

EP 1852824 11/2007
EP 2459074 B1 * 7/2018 ............... A61B 8/12
(Continued)

OTHER PUBLICATIONS

Bhakta, Deepak, and John M Miller. "Principles of electroanatomic mapping." Indian pacing and electrophysiology journal vol. 8,1 32-50. Feb. 1, 2008 (Year: 2008).*
(Continued)

*Primary Examiner* — Joel Lamprecht
*Assistant Examiner* — James F McDonald, III
(74) *Attorney, Agent, or Firm* — Smith, Gambrell & Russell LLP

(57) ABSTRACT

In one exemplary mode, a medical system includes an ultrasound probe configured to captured ultrasonic images of at least part of a body part of a living subject, a display, and a processor configured to render to the display respective representations of respective electro-anatomical data subsets superimposed over respective ones of the ultrasonic images.

17 Claims, 6 Drawing Sheets

(51) Int. Cl.
*A61B 8/08* (2006.01)
*A61B 8/12* (2006.01)
*A61M 25/01* (2006.01)

(52) U.S. Cl.
CPC ......... *A61B 8/461* (2013.01); *A61M 25/0105* (2013.01); *A61B 2562/0223* (2013.01); *A61M 2025/0166* (2013.01)

(56) References Cited

U.S. PATENT DOCUMENTS

| | | | | |
|---|---|---|---|---|
| 6,239,724 | B1 | 5/2001 | Doron et al. | |
| 6,266,551 | B1 | 7/2001 | Osadchy et al. | |
| 6,332,089 | B1 | 12/2001 | Acker et al. | |
| 6,484,118 | B1 | 11/2002 | Govari | |
| 6,618,612 | B1 | 9/2003 | Acker et al. | |
| 6,690,963 | B2 | 2/2004 | Ben-Haim et al. | |
| 6,716,166 | B2 | 4/2004 | Govari | |
| 6,773,402 | B2 | 8/2004 | Govari et al. | |
| 7,756,576 | B2 | 7/2010 | Levin | |
| 7,848,787 | B2 | 12/2010 | Osadchy | |
| 7,869,865 | B2 | 1/2011 | Govari et al. | |
| 8,075,486 | B2 | 12/2011 | Tal | |
| 9,011,340 | B2 | 4/2015 | Tal | |
| 10,653,318 | B2 * | 5/2020 | Welsh | A61B 5/0044 |
| 10,835,207 | B2 | 11/2020 | Altmann et al. | |
| 10,918,310 | B2 | 2/2021 | Cohen et al. | |
| 11,123,046 | B1 | 9/2021 | Zohar et al. | |
| 11,206,984 | B1 * | 12/2021 | Boveja | A61B 5/0082 |
| 2002/0065455 | A1 | 5/2002 | Ben-Haim et al. | |
| 2003/0120150 | A1 | 6/2003 | Govari | |
| 2004/0068178 | A1 | 4/2004 | Govari | |
| 2006/0241445 | A1 * | 10/2006 | Altmann | A61B 8/543 600/443 |
| 2006/0253030 | A1 * | 11/2006 | Altmann | G06T 17/00 600/466 |
| 2007/0055150 | A1 * | 3/2007 | Donaldson | A61B 8/5238 600/459 |
| 2008/0009758 | A1 * | 1/2008 | Voth | A61B 5/367 600/523 |
| 2008/0137927 | A1 * | 6/2008 | Altmann | A61B 5/339 382/131 |
| 2009/0069704 | A1 * | 3/2009 | MacAdam | A61B 5/339 600/523 |
| 2011/0152684 | A1 * | 6/2011 | Altmann | A61B 8/5238 600/443 |
| 2013/0245433 | A1 * | 9/2013 | Deladi | A61B 8/445 600/424 |
| 2014/0243641 | A1 * | 8/2014 | Boveja | A61B 6/5247 600/374 |
| 2018/0160978 | A1 * | 6/2018 | Cohen | A61B 18/1492 |
| 2019/0060003 | A1 | 2/2019 | Tuason | |
| 2019/0200886 | A1 * | 7/2019 | Welsh | A61B 34/20 |
| 2019/0313910 | A1 * | 10/2019 | Vignon | A61B 5/066 |
| 2019/0314002 | A1 | 10/2019 | Peterson et al. | |
| 2020/0155114 | A1 | 5/2020 | Park et al. | |
| 2020/0214662 | A1 * | 7/2020 | Konofagou | A61B 8/4416 |
| 2021/0100535 | A1 | 4/2021 | Kumar et al. | |
| 2021/0100612 | A1 | 4/2021 | Baron et al. | |
| 2021/0169394 | A1 * | 6/2021 | Chou | A61B 34/10 |
| 2021/0251545 | A1 | 8/2021 | Erasala et al. | |

FOREIGN PATENT DOCUMENTS

| | | |
|---|---|---|
| WO | WO9605768 | 2/1996 |
| WO | WO2019141526 | 7/2019 |

OTHER PUBLICATIONS

Banchs, Javier E. et al., "Intracardiac echocardiography in complex cardiac catheter ablation procedures", Journal of Interventional Cardiac Electrophysiology, Kluwer Academic Publishers, BO, vol. 23, No. 3, May 18, 2010, pp. 167-184.

Proietti, Riccardo et al., "Intracardiac echo-facilitated 3D electroanatomical mapping of ventricular arrhythmias from the papillary muscles: assessing the 'fourth dimension' during ablation", EUROPACE, Aug. 2, 2016, pp. 21-28.

International Search Report mailed Jun. 26, 2023 from corresponding PCT Application No. PCT/IB2023/052566.

* cited by examiner

44

INTRACARDIAC IMAGING USING ELECTRO-ANATOMICAL DATA TO GENERATE AUGMENTED ULTRASONIC IMAGES

FIELD OF THE DISCLOSURE

The present disclosure relates to medical systems, and in particular, but not exclusively to, augmented imaging.

BACKGROUND

A variety of devices and methods for intracardiac ultrasonic imaging are known in the art. For example, Biosense Webster Inc. (Irvine, California) offers the CartoSound™ software module and SoundStar™ catheter for producing 2D ultrasound images in real time. The SoundStar catheter, which is inserted through the vascular system into the heart, contains a position sensor and a phased array ultrasound transducer. The CartoSound software module processes the signals from the position sensor and the ultrasound transducer to generate 3D images of the heart chambers.

U.S. Pat. No. 8,075,486 of Tal describes using specialized cardiac catheters for image acquisition, features of the heart are readily identifiable on an ultrasound image, based on a previously generated electrical activation map of the heart. The electrical activation map is automatically registered with the ultrasound image using information obtained from position sensors in the catheters. Features identifiable on the electrical activation map, presented as points, tags, design lines, and textual identification, are projected into the plane of the ultrasound fan and overlaid on the ultrasound image, thereby clarifying the features that are visible on the latter.

BRIEF DESCRIPTION OF THE DRAWINGS

The present disclosure will be understood from the following detailed description, taken in conjunction with the drawings in which.

DESCRIPTION OF EXAMPLES

Overview

Figure 1:
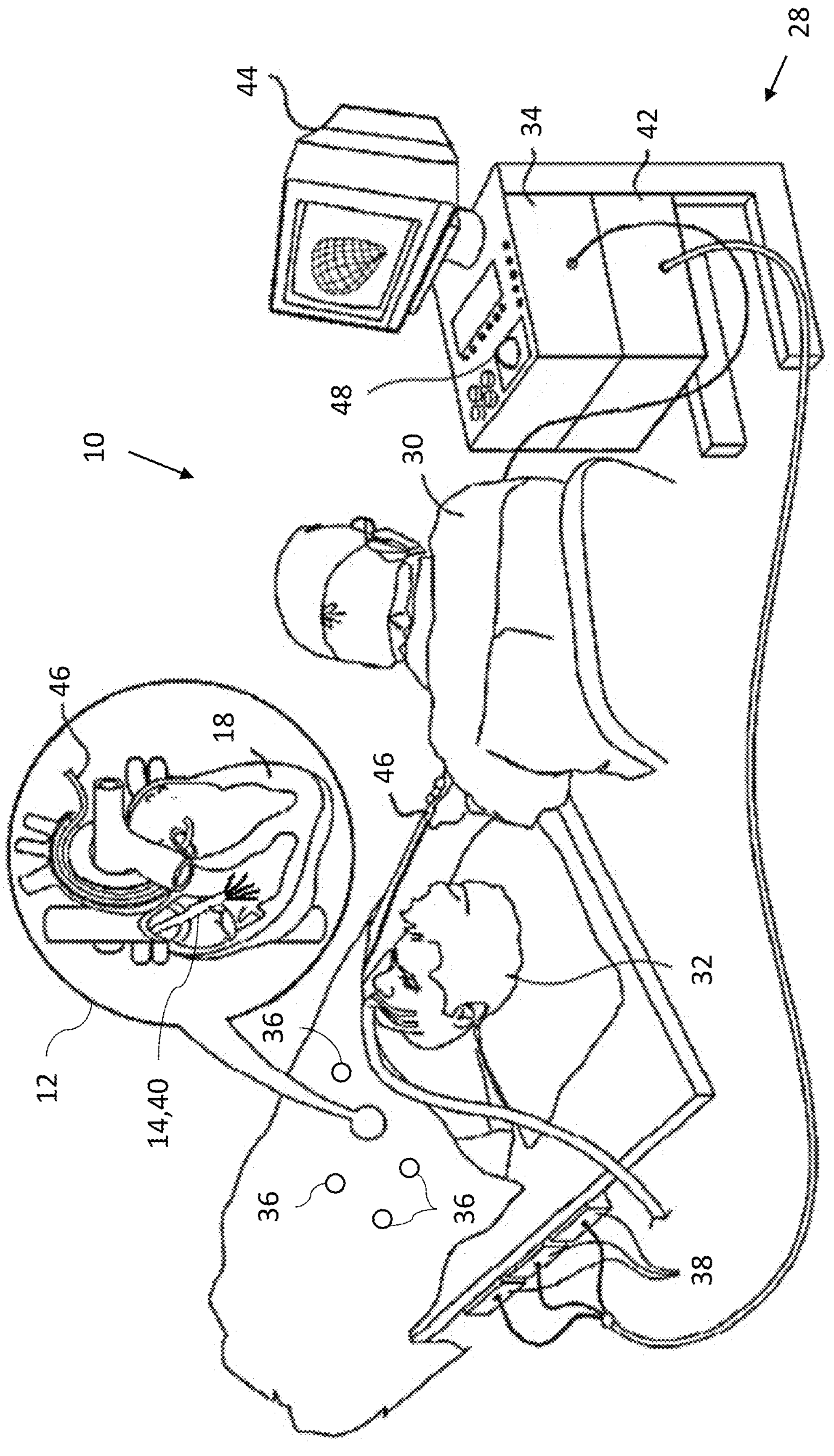
FIG. 1 is a schematic, pictorial illustration of a catheter-based system including ultrasonic imaging, in accordance with an exemplary mode of the present disclosure.

Ultrasound scans (e.g., two-dimensional (2D) or three-dimensional (3D) ultrasonic images) enable a physician to view movement of a chamber of the heart (or other body part) in real time. Electro-anatomical data for the chamber (or other body part), for example local activation times (LATs), are typically presented as LAT values (e.g., using an appropriate color scheme) overlayed on a 3D anatomical map of the chamber. However, the 3D electro-anatomical map may not represent an image of the chamber of the heart and may not provide a real-time representation showing movement of the chamber of the heart. At present, the physician often needs to look at both presentations, i.e., ultrasound and a 3D electro-anatomical maps separately, and mentally formulate a relationship between the two presentations. This process requires mental energy and has the potential lead to errors of judgment.

Exemplary modes of the present disclosure solve the above problems by superimposing representations of electro-anatomical data over ultrasonic images captured by an ultrasound probe such that electro-anatomical data and real-time ultrasound imagery may be assessed in a single view. The electro-anatomical data may include LAT values, bipolar data, and/or propagation data such as velocity vectors. The electro-anatomical data may be represented using colored or shaded lines or regions (e.g., to represent LAT values or bipolar data) or arrows (e.g., to represent propagation data). The representations of the electro-anatomical data may be superimposed over 2D ultrasonic images (e.g., 2D ultrasonic slices) or within (and/or over) 3D ultrasonic images.

The electro-anatomical data to be included in respective ultrasonic images is selected based on the electro-anatomical data being positioned within, or within a threshold proximity to, the respective ultrasonic images with respect to a 3D coordinate space. For example, data from a 3D electro-anatomical map may be selected for superimposing over the respective ultrasonic images based on where the respective ultrasonic images intersect the 3D electro-anatomical map in a 3D coordinate space. For example, if the 3D electro-anatomical map includes a certain distribution of colors representing LAT values (or bipolar data), then the coloring used in the 3D electro-anatomical map at the intersection of the 3D electro-anatomical map and the 2D ultrasonic image is superimposed as one or more lines on the 2D ultrasonic image to show the LAT values (or bipolar data) relevant for that 2D ultrasonic image.

The display is dynamic so as the ultrasound probe is moved and captures different ultrasonic images of the chamber of the heart, the representations of the electro-anatomical data superimposed over the different ultrasonic images changes to reflect the new positions of the different ultrasonic images in the 3D coordinate space and the new electro-anatomical data now included within, or within a given threshold proximity to, the different ultrasonic images. For example, as the ultrasound probe is moved, the LAT values superimposed over the ultrasonic images move and change to reflect the current LAT values in the current region of 3D coordinate space occupied by the respective ultrasonic images.

The representations of electro-anatomical data superimposed over the ultrasonic images need not be restricted to electro-anatomical data included in the 3D electro-anatomical map. Other electro-anatomical data not used in the 3D electro-anatomical map may have been collected by a mapping catheter. For example, electro-anatomical data (e.g., bipolar data) captured from tissue of internal structures such as papillary muscle may not be included in the 3D electro-anatomical map. However, representations of the electro-anatomical data captured from the tissue of internal structures may be superimposed over respective ultrasonic images. In this manner, electro-anatomical data which is not normally seen by the physician (due to it being excluded from the 3D electro-anatomical map) is now included in respective ultrasonic images.

In some exemplary modes, the position of a distal end of a catheter inserted into the chamber of the heart may be tracked, and a representation of the distal end of the tracked catheter may be superimposed over respective ultrasonic images.

SYSTEM DESCRIPTION

Figure 2:
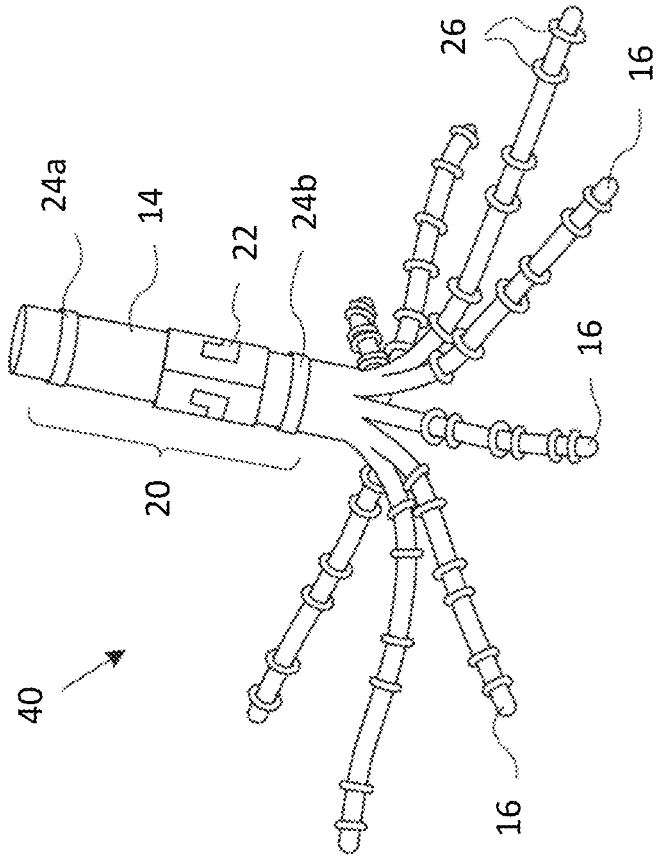
FIG. 2 is a schematic side view of the distal end of a mapping catheter used in the system of FIG. 1.

Reference is now made to FIG. 1, which is a schematic, pictorial illustration of a catheter-based system 10 including ultrasonic imaging, in accordance with an exemplary mode of the present disclosure. Reference is also made to FIG. 2, which is a schematic side view of the distal end of a mapping catheter 40 used in the system 10 of FIG. 1.

The system 10 is used to determine the position of the catheter 40, seen in an inset 12 of FIG. 1 and in more detail in FIG. 2. The catheter 40 is a probe which includes a shaft 14 and a plurality of deflectable arms 16 (only some labeled for the sake of simplicity) for inserting into a body-part (e.g., chamber of a heart 18) of a living subject. The deflectable arms 16 have respective proximal ends connected to the distal end of the shaft 14.

The catheter 40 includes a position sensor 20 disposed on the shaft 14 in a predefined spatial relation to the proximal ends of the deflectable arms 16. The position sensor 20 may include a magnetic sensor 22 and/or at least one shaft electrode 24. The magnetic sensor 22 may include at least one coil, for example, but not limited to, a dual-axis or a triple axis coil arrangement to provide position data for location and orientation including roll. The catheter 40 includes multiple electrodes 26 (only some labeled in FIG. 2 for the sake of simplicity) disposed at different, respective locations along each of the deflectable arms 16. Typically, the catheter 40 may be used for mapping electrical activity in a heart of the living subject using the electrodes 26, or for performing any other suitable function in a body-part of a living subject, for example, but not limited to, reversible and/or irreversible electroporation and/or RF ablation.

The medical procedure system 20 may determine a position and orientation of the shaft 14 of the catheter 40 based on signals provided by the magnetic sensor 22 and/or the shaft electrodes 24 (proximal-electrode 24*a* and distal-electrode 24*b*) fitted on the shaft 14, on either side of the magnetic sensor 22. The proximal-electrode 24*a*, the distal-electrode 24*b*, the magnetic sensor 22 and at least some of the electrodes 26 are connected by wires running through the shaft 14 to various driver circuitries in a console 28. In some exemplary modes, the distal-electrode 24*b* and/or the proximal electrode 24*a* may be omitted.

The illustration shown in FIG. 2 is chosen purely for the sake of conceptual clarity. Other configurations of shaft electrodes 24 and electrodes 26 are possible. Additional functionalities may be included in the position sensor 20. Elements which are not relevant to the disclosed exemplary modes of the disclosure, such as irrigation ports, are omitted for the sake of clarity.

A physician 30 navigates the catheter 40 to a target location in a body part (e.g., the heart 18) of a patient 32 by manipulating the shaft 14 using a manipulator near the proximal end of the catheter 40 and/or deflection from a sheath. The catheter 40 is inserted through the sheath, with the deflectable arms 16 gathered together, and only after the catheter 40 is retracted from the sheath, the deflectable arms 16 are able to spread and regain their intended functional shape. By containing deflectable arms 16 together, the sheath also serves to minimize vascular trauma on its way to the target location.

Console 28 comprises processing circuitry 34, typically a general-purpose computer and a suitable front end and interface circuits for generating signals in, and/or receiving signals from, body surface electrodes 36 which are attached by wires (not shown) running through a cable (not shown) to the chest and to the back, or any other suitable skin surface, of the patient 32.

Console 28 further comprises a magnetic-sensing subsystem. The patient 32 is placed in a magnetic field generated by a pad containing at least one magnetic field radiator 38, which is driven by a unit 42 disposed in the console 28. The magnetic field radiator(s) 38 is configured to transmit alternating magnetic fields into a region where the body-part (e.g., the heart 18) is located. The magnetic fields generated by the magnetic field radiator(s) 38 generate direction signals in the magnetic sensor 22. The magnetic sensor 22 is configured to detect at least part of the transmitted alternating magnetic fields and provide the direction signals as corresponding electrical inputs to the processing circuitry 34.

In some exemplary modes, the processing circuitry 34 uses the position-signals received from the shaft electrodes 24, the magnetic sensor 22 and the electrodes 26 to estimate a position of the catheter 40 inside an organ, such as inside a cardiac chamber. In some exemplary modes, the processing circuitry 34 correlates the position signals received from the electrodes 24, 26 with previously acquired magnetic location-calibrated position signals, to estimate the position of the catheter 40 inside the organ. The position coordinates of the shaft electrodes 24 and the electrodes 26 may be determined by the processing circuitry 34 based on, among other inputs, measured impedances, or on proportions of currents distribution, between the electrodes 24, 26 and the body surface electrodes 36. The console 28 drives a display 44, which may show the distal end of the catheter 40 inside the heart 18.

The method of position sensing using current distribution measurements and/or external magnetic fields is implemented in various medical applications, for example, in the Carto® system, produced by Biosense Webster Inc. (Irvine, California), and is described in detail in U.S. Pat. Nos. 5,391,199, 6,690,963, 6,484,118, 6,239,724, 6,618,612, 6,332,089, 7,756,576, 7,869,865, and 7,848,787, in PCT Patent Publication WO 96/05768, and in U.S. Patent Application Publications 2002/0065455 A1, 2003/0120150 A1 and 2004/0068178 A1.

The Carto® 3 system applies an Active Current Location (ACL) impedance-based position-tracking method. In some exemplary modes, using the ACL method, the processing circuitry 34 is configured to create a mapping (e.g., current-position matrix (CPM)) between indications of electrical impedance and positions in a magnetic coordinate frame of the magnetic field radiator(s) 38. The processing circuitry 34 estimates the positions of the shaft electrodes 24 and the electrodes 26 by performing a lookup in the CPM.

Other methods of determining the location of the distal end of the catheter 40 may be used, for example, based on ultrasonic transducers and receivers, using imaging techniques such as ultrasound or MRI or CT scans which may include disposing radiopaque tags on the catheter 40.

Processing circuitry 34 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

FIG. 1 shows only elements related to the disclosed techniques, for the sake of simplicity and clarity. The system 10 typically comprises additional modules and elements that are not directly related to the disclosed techniques, and thus are intentionally omitted from FIG. 1 and from the corresponding description.

The catheter 40 described above includes eight deflectable arms 16 with six electrodes 26 per arm 16. Any suitable catheter may be used instead of the catheter 40, for example, a catheter with a different number of flexible arms and/or electrodes per arm, or a different probe shape such as a balloon catheter or basket catheter or a lasso catheter, by way of example only.

The system 10 may also perform electroporation or RF ablation (or other ablation technique) of heart tissue using any suitable catheter, for example using the catheter 40 or a different catheter and any suitable ablation method. The console 28 may include a signal generator configured to generate an electrical signal to be applied by an electrode or electrodes of a catheter connected to the console 28, (and optionally one or more of the body surface electrodes 36), to perform electroporation or RF ablation of a myocardium of the heart 18. The console 28 may include a pump (not shown), which pumps irrigation fluid into an irrigation channel to a distal end of a catheter performing RF ablation. The catheter performing the RF ablation may also include temperature sensors (not shown) which are used to measure a temperature of the myocardium during RF ablation and regulate an ablation power and/or an irrigation rate of the pumping of the irrigation fluid according to the measured temperature.

Figure 3:
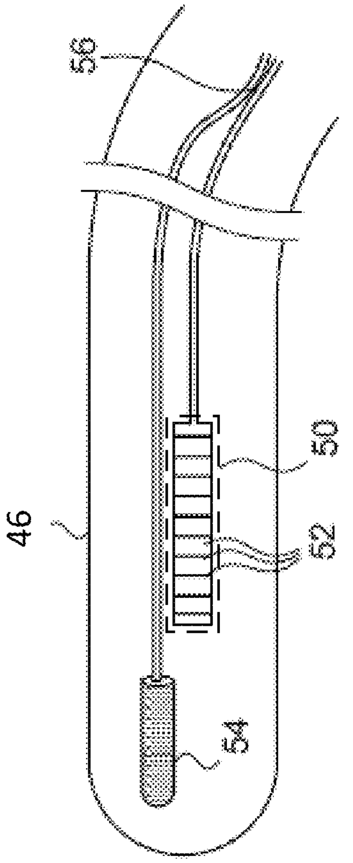
FIG. 3 is a schematic side view of the distal end of an ultrasound probe used in the system of FIG. 1.

Reference is now made to FIG. 3, which is a schematic side view of the distal end of an ultrasound probe 46 used in the system 10 of FIG. 1. Reference is also made to FIG. 1.

System 10 and ultrasound probe 46 are shown here by way of illustration, to assist in understanding the methods of ultrasound-based imaging that are described further below. These methods, however, are not limited to catheter-based ultrasonic sensing and may similarly be applied, mutatis mutandis, using 2D or 3D ultrasound images acquired by other types of probes, both intra- and extra-corporeal. Furthermore, these methods may be used in mapping of other anatomical cavities, not only in the heart. The ultrasound probe 46 is configured to captured ultrasonic images of at least part of a body part (e.g., the heart 18) of a living subject (e.g., patient 32).

As shown in FIG. 1, the physician 30, inserts ultrasound probe 46 into the body of the patient 32, so that the distal end of the ultrasound probe 46 passes through the vascular system into the patient's heart 18. The ultrasound probe 46 is connected at its proximal end to the console 28. The processing circuitry 34 receives and processes signals from ultrasound probe 46, as described hereinbelow. The processing circuitry 34 may comprise a general-purpose computer processor, which is programmed in software to carry out the functions that are described herein. This software may be downloaded to the processor in electronic form, over a network, for example. Alternatively, or additionally, the software may be stored on tangible computer-readable storage media, such as optical, magnetic, or electronic memory media. Further additionally or alternatively, at least some of the functions of the processor may be carried out by a digital signal processor (DSP) or by dedicated or programmable hardware logic circuits.

Typically, console 28 also enables a user to observe and regulate the functions of ultrasound probe 46 and to view and edit images that are formed using ultrasound probe 46. For these purposes, the console 28 comprises display 44 and a user interface 48.

As shown in FIG. 3, the distal end of ultrasound probe 46 comprises an ultrasound imaging device 50, which is used to produce ultrasound images of the inside of the body. Device 50 typically comprises a phased array of transducers 52, which is operated, as is known in the art, so as to capture a two-dimensional (2D) "fan" image in the plane of the scanning ultrasonic beam (referred to herein as the "beam plane" or "image plane"), which contains the longitudinal axis of the ultrasound probe 46. The transducers 52 receive ultrasonic waves that are reflected from objects in the beam plane and output signals in response to the reflected waves. Typically, these signals are conveyed by wires 56 running through ultrasound probe 46 to console 28, which processes the signals in order to form and display ultrasound images, as described hereinbelow.

The distal end of ultrasound probe 46 further comprises a position sensor 54, which generates signals that indicate the position (location and orientation including roll) of the catheter within the body. Based on these position signals, console 28 determines the location and orientation of each fan image captured by imaging device 50. Processing circuitry 34 is thus able to determine the coordinates of objects appearing in the fan image and the boundaries of the fan image.

In the pictured exemplary mode, system 10 uses magnetic position sensing to determine position coordinates of the distal end of ultrasound probe 46 inside heart 18. To determine the position coordinates, a driver circuit in console 28 drives magnetic field radiators 38 to generate magnetic fields within the body of patient 32. Typically, magnetic field radiator 38 comprise coils, which are placed below the patient's torso at known positions external to the body. These coils generate magnetic fields in a predefined working volume that contains heart 18. Sensor 54, which may comprise, for example, a magnetic position sensor including one or more coils within the distal end of ultrasound probe 46, generates electrical signals in response to these magnetic fields. The processing circuitry 34 processes these signals in order to determine the position (location and orientation) coordinates of the distal end of ultrasound probe 46. Console 28 may use the coordinates in driving display 44 to show the location and status of the ultrasound probe 46.

This method of position sensing and processing is implemented in the CARTO® 3 system produced by Biosense Webster Inc. This sort of magnetic position sensing is described in detail, for example, in U.S. Pat. No. 6,266,551. Other systems that combine ultrasonic imaging with magnetic position sensing are described in U.S. Pat. Nos. 6,690,963, 6,716,166 and 6,773,402.

Although FIG. 1 shows a particular system configuration, other system configurations may be used in alternative exemplary modes of the present disclosure. For example, the methods described hereinbelow may be applied using position transducers of other types, such as impedance-based or ultrasonic position sensors. The term "position transducer" as used herein refers to an element mounted on or in ultrasound probe 46 that causes console 28 to receive signals indicative of the coordinates of the element. The position transducer may thus comprise a receiver in the ultrasound probe 46, such as sensor 54, which generates a position signal to the control unit based on energy received by the transducer; or it may comprise a transmitter, emitting energy that is sensed by a receiver external to the probe. Furthermore, the methods described hereinbelow may similarly be applied in mapping and imaging applications using not only catheters type-probes, but also probes of other types, both in the heart and in other body organs and regions, as well as ultrasound probes external to the body.

Figure 4:
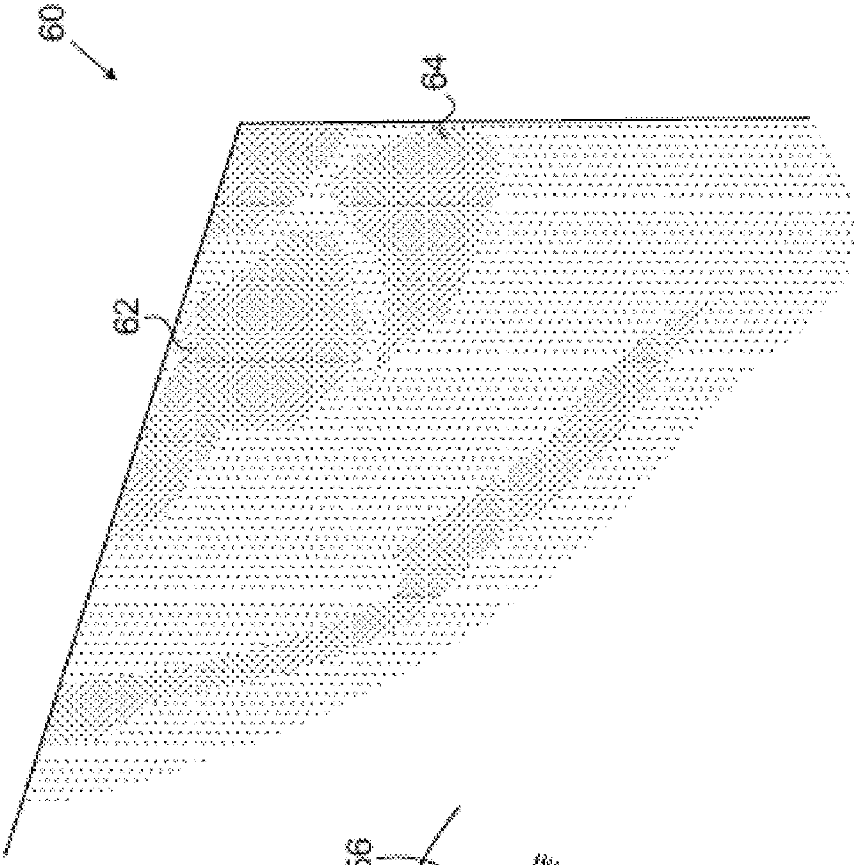
FIG. 4 is a schematic representation of an ultrasonic image captured by the ultrasound probe of the system of FIG. 1.

Reference is now made to FIG. 4, which is a schematic representation of an ultrasonic image 60 captured by the ultrasound probe 46 of the system 10 of FIG. 1.

The image has the form of a 2D fan, with its vertex at imaging device 50. As noted above, console 28 can determine the location of the vertex and the orientation of the fan in 3D space (including the boundaries of the fan) based on the signals received from position sensor 54. Dark areas 62, 64 in the image correspond to areas, such as the heart chambers, that are filled with blood and therefore have low reflectance. Brighter areas generally represent tissue, such as the internal and external heart walls.

As noted earlier, physician 30 may manipulate ultrasound probe 46 inside heart 18 to capture images from different locations and at different orientations. The reflections that make up the images may originate not only from the heart chamber in which the distal end of the ultrasound probe 46 is located, but also from other heart chambers and anatomical structures. Thus, for example, ultrasound probe 46 may be inserted into the right atrium (which is relatively easy to access via the vena cava) and may capture images from the right atrium of the left atrium and possibly the ventricles.

Figure 5:
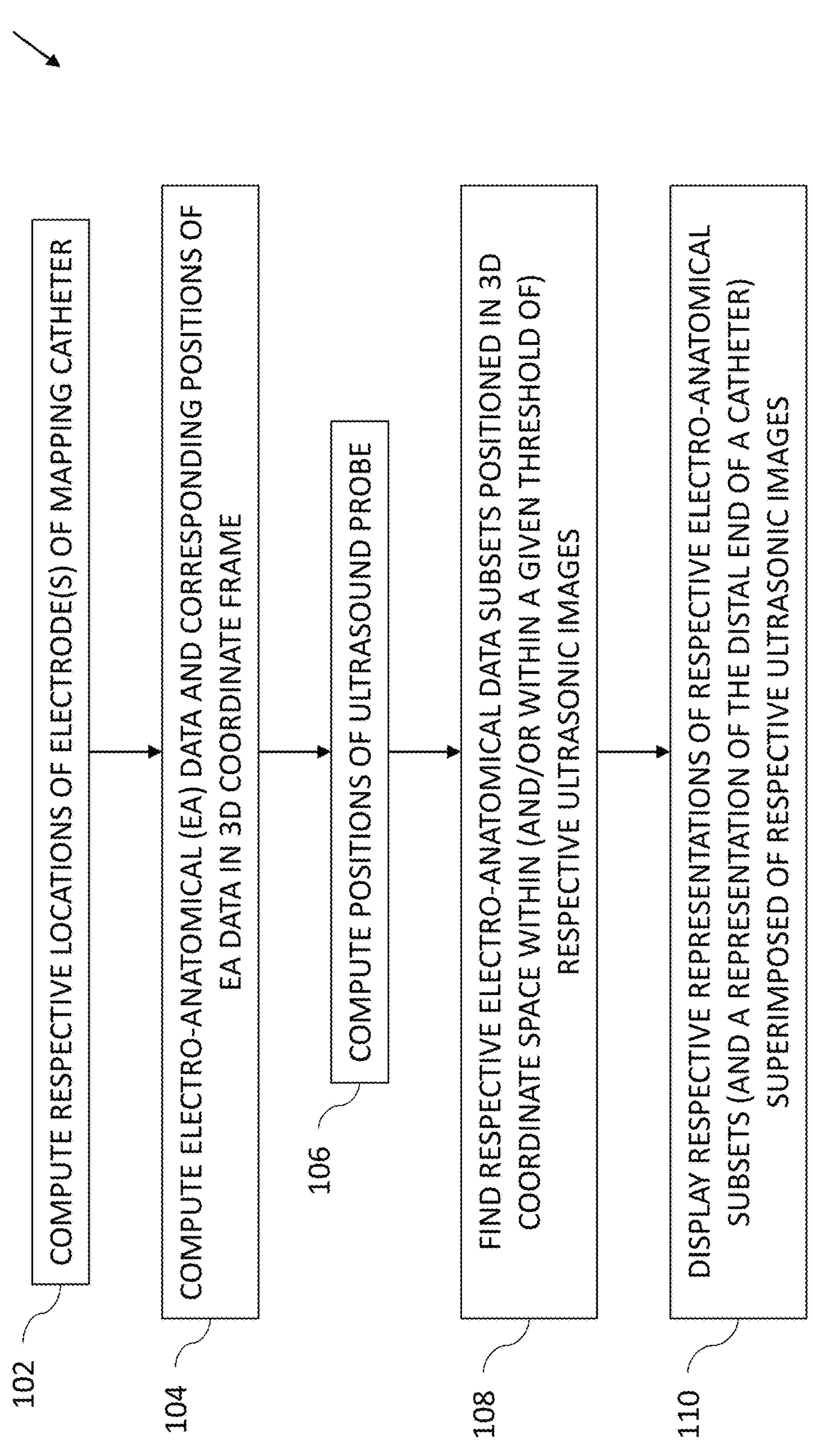
FIG. 5 is a flow chart including steps in a method of operation of the system of FIG. 1.

Reference is now made to FIG. 5, which is a flow chart 100 including steps in a method of operation of the system 10 of FIG. 1.

The mapping catheter 40 is configured to be inserted into the body part. The mapping catheter 40 includes the electrodes 26 configured to capture electrical activity from tissue of the body part (e.g., chamber of the heart 18) at respective locations in the body part over time. In some exemplary modes, the mapping catheter 40 may include one or more electrodes to capture the electrical activity from the tissue of the body part. The mapping catheter 40 is moved around the body part (e.g., around the chamber of the heart 18) to collect electrical activity at different respective locations.

The system 10 includes at least one position sensor (e.g., the position sensor 20, the electrodes 26, the magnetic sensor 22, the shaft electrodes 24, the position sensor 54, and/or the body surface electrodes 36) configured to provide at least one signal indicative of positions of the ultrasound probe 46 and the respective locations of the electrode(s) 26 of the mapping catheter 40 over time. The position(s) may be disposed on the ultrasound probe 46 and/or the mapping catheter 40, and/or on another probe inside the body or outside the body. In some exemplary modes, the position sensor(s) comprise: the magnetic sensor(s) 22 disposed on the mapping catheter 40 and the (magnetic) position sensor (s) 54 disposed on the ultrasound probe 46. In some exemplary modes, the position sensor may include an ultrasonic transducer.

The processing circuitry 34 is configured to compute the respective locations of the electrode(s) 26 in a 3D coordinate frame responsively to the signal(s) provided by the position sensor(s) (e.g., the position sensor 20, the electrodes 26, the magnetic sensor 22, the shaft electrodes 24, and/or the body surface electrodes 36) (block 102). The computed respective locations of the electrode(s) 26 are locations at which electrical activity of the tissue is captured (e.g., for inclusion in a 3D anatomical map). The respective locations may be computed based on magnetic tracking, impedance-based tracking, a combination of magnetic and impedance-based tracking, ultrasound tracking or any suitable tracking modality, as described above in more detail with reference to FIG. 1.

The processing circuitry 34 is configured to compute the electro-anatomical data (comprised in an electro-anatomical dataset) responsively to the capture electrical activity, and corresponding positions of the electro-anatomical data (e.g., in the 3D coordinate frame) responsively to the computed respective locations (block 104). The electro-anatomical data may include any one or more of the following: local activation time data; bipolar data; propagation data; and velocity vectors.

The ultrasound probe 46 is inserted into the body-part and maneuvered as needed around the body part. The processing circuitry 34 is configured to compute positions of the ultrasound probe 46 responsively to the signal(s) provided by the position sensor(s) (e.g., the position sensor 54 and/or the body surface electrodes 36 or any suitable sensor or transducer) (block 106) as described in more detail with reference to FIG. 3. The processing circuitry 34 is configured to compute the positions (e.g., boundaries) of the respective ultrasonic images captured at the respective computed positions of the ultrasound probe 46 as described in more detail with reference to FIGS. 3 and 4.

The processing circuitry 34 is configured to find respective electro-anatomical data subsets from the electro-anatomical dataset (computed in the step of block 104) having electro-anatomical data positioned in three-dimension (3D) coordinate space within the respective ones of the ultrasonic images, and/or within a given threshold of, the respective ultrasonic images (block 108) (e.g., based on the positions of the electro-anatomical data in the 3D coordinate space and the positions (e.g., boundaries) of the respective ultrasonic images in the 3D coordinate space). In other words, for each ultrasonic image, the processing circuitry 34 is configured to find an electro-anatomical data subset from the electro-anatomical dataset having electro-anatomical data positioned within, or within a given threshold of, that ultrasonic image in the 3D coordinate space. The threshold may be set to any suitable default value, for example, in the range of 0.5 mm to 2 mm for optional adjustment by the physician. The electro-anatomical data subsets may include any one or more of the following: local activation time data; bipolar data; propagation data; and velocity vectors. In some exemplary modes, each ultrasound image is a two-dimensional (2D) slice. In some exemplary modes, each ultrasound image is a three-dimensional (3D) image.

Figure 6:
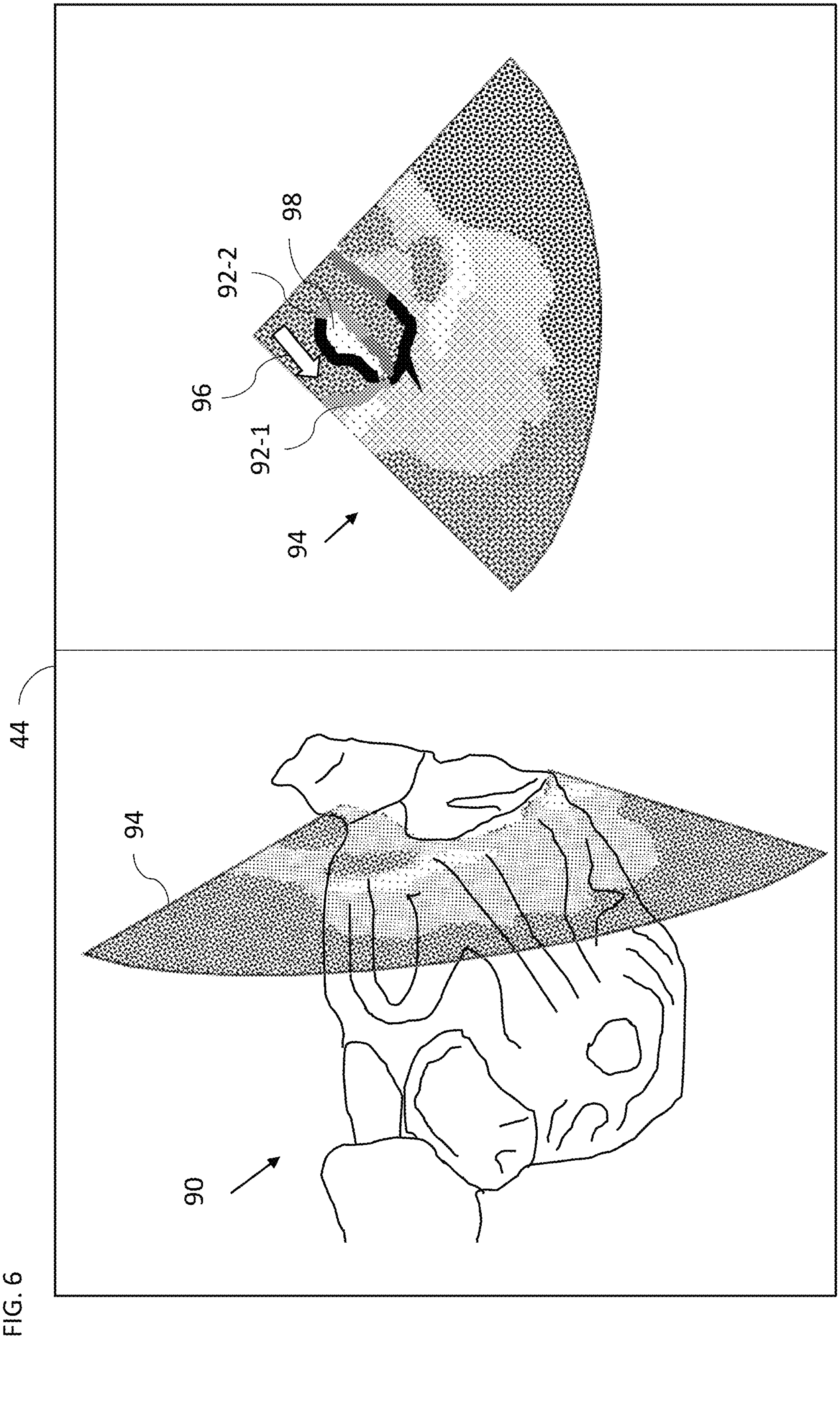
FIG. 6 is a schematic view of a 3D anatomical map and a 2D ultrasonic image with representations of electro-anatomical data disposed thereon.

Reference is now made to FIG. 6, which is a schematic view of a 3D anatomical map 90 and a 2D ultrasonic image 94 with representations 92 of electro-anatomical data disposed thereon. Reference is also made to FIG. 5.

The right-hand side of the display 44 shown in FIG. 6 shows a 2D ultrasonic image 94 captured by the ultrasound probe 46. The representations 92 of electro-anatomical data may be colored and/or shaded and/or patterned to reflect different values of electro-anatomical data (e.g., LAT values or bipolar data values).

In some exemplary modes, data from a 3D electro-anatomical map may be selected for superimposing over the 2D ultrasonic image 94 based on where the 2D ultrasonic image 94 intersects the 3D electro-anatomical map in the 3D coordinate space. For example, if the 3D electro-anatomical map includes a certain distribution of colors representing LAT values (or bipolar data), then the coloring used in the 3D electro-anatomical map at the intersection of the 3D electro-anatomical map and the 2D ultrasonic image 94 (in the 3D coordinate space) is superimposed as one or more lines 92-1 on the 2D ultrasonic image 94 to show the LAT values (or bipolar data) relevant for the 2D ultrasonic image 94. The lines may be thicker than the corresponding coloring on the 3D electro-anatomical map at the intersection of the 3D electro-anatomical map and the 2D ultrasonic image 94.

As the ultrasound probe 46 is moved and captures different ultrasonic images of the chamber of the heart 18, the representations of the electro-anatomical data superimposed over the different ultrasonic images are changed to reflect the new positions of the different ultrasonic images being displayed and the new electro-anatomical data now included within, or within a given threshold proximity to, the different ultrasonic images. For example, as the ultrasound probe 46 is moved, the LAT values superimposed over the ultrasonic images move and change to reflect the current LAT values in the current region of 3D coordinate space occupied by the respective ultrasonic images.

The representations 92 of electro-anatomical data superimposed over the ultrasonic image 94 need not be restricted to electro-anatomical data included in the 3D electro-anatomical map. Other electro-anatomical data not used in the 3D electro-anatomical map may have been collected by a mapping catheter. For example, electro-anatomical data (e.g., bipolar data) captured from tissue of internal structures 98 such as papillary muscle may not be included in the 3D electro-anatomical map. However, representations 92-2 of the electro-anatomical data captured from the tissue of internal structures 98 may be superimposed over the 2D ultrasonic image 94 as shown in FIG. 6. In this manner, electro-anatomical data which is not normally seen by the physician (due to it being excluded from the 3D electro-anatomical map) is now included in the ultrasonic images.

In some exemplary modes, the position of a distal end of a catheter inserted into the chamber of the heart 18 may be tracked (as described in more detail with reference to FIG. 1), and a representation 96 of the distal end of the tracked catheter may be superimposed over the 2D ultrasonic images 94.

Therefore, the processing circuitry 34 is configured to render to the display 44 respective representations 92 of respective electro-anatomical data subsets superimposed over respective ultrasonic images 94 (block 110) (in other words, each ultrasonic image 94 has its own representations 92 of its own corresponding electro-anatomic data subset superimposed over it). The respective positions of the representations 92 in the respective ultrasonic images 94 are computed based on the corresponding positions of the electro-anatomical data that the representations 92 are representing. In some exemplary modes, the processing circuitry 34 is configured to render to the display 44 the respective representations 92 of the respective electro-anatomical data subsets and a representation 96 of a distal end of a catheter superimposed over the respective ultrasonic images 94. The respective representations 92 may include respective multi-colored lines or multi-colored regions. The multi-colored lines or multi-colored regions represent local activation times or bipolar data.

In some exemplary modes, the processing circuitry 34 is configured to render to the display 44 the representation(s) 92 of a respective electro-anatomical data subset superimposed over the 2D ultrasonic image 94 including internal structure(s) 98 of the chamber of the heart 18 with at least some of the representations 92 indicating electro-anatomical data (e.g., bipolar data) of the internal structure 98 (e.g., a papillary muscle).

The left-hand side of the display 44 shows the 3D anatomical map 90 (for example, generated from points captured by the mapping catheter 40 or from data captured by the ultrasound probe 46). The 3D anatomical map 90 may be computed using any suitable map generation method, for example, using fast anatomical mapping (FAM) to form a smooth shell described in U.S. Pat. No. 10,918,310 to Cohen, et al. from points captured by the mapping catheter 40, or Fast anatomical mapping using ultrasound images described in U.S. Pat. No. 10,835,207 to Altmann, et al., from data captured by the ultrasound probe 46. The 2D ultrasonic image 94 is also shown intersecting the 3D anatomical map 90. The 2D ultrasonic image 94 is positioned with respect to the 3D anatomical map 90 according to the respective positions of the 3D anatomical map 90 and the 2D ultrasonic image 94 in the 3D coordinate space according to the positions provided by the position sensor 54 and the associated position tracking system. The 2D ultrasonic image 94 is shown as being partially transparent so that the orientation of the 2D ultrasonic image 94 with respect to the 3D anatomical map 90 can be seen clearly. In some exemplary modes, the 2D ultrasonic image 94 is shown as being opaque over the 3D anatomical map 90. In some exemplary modes, the 3D anatomical map 90 is shown without the 2D ultrasonic image 94 overlaying the 3D anatomical map 90.

Figure 7:
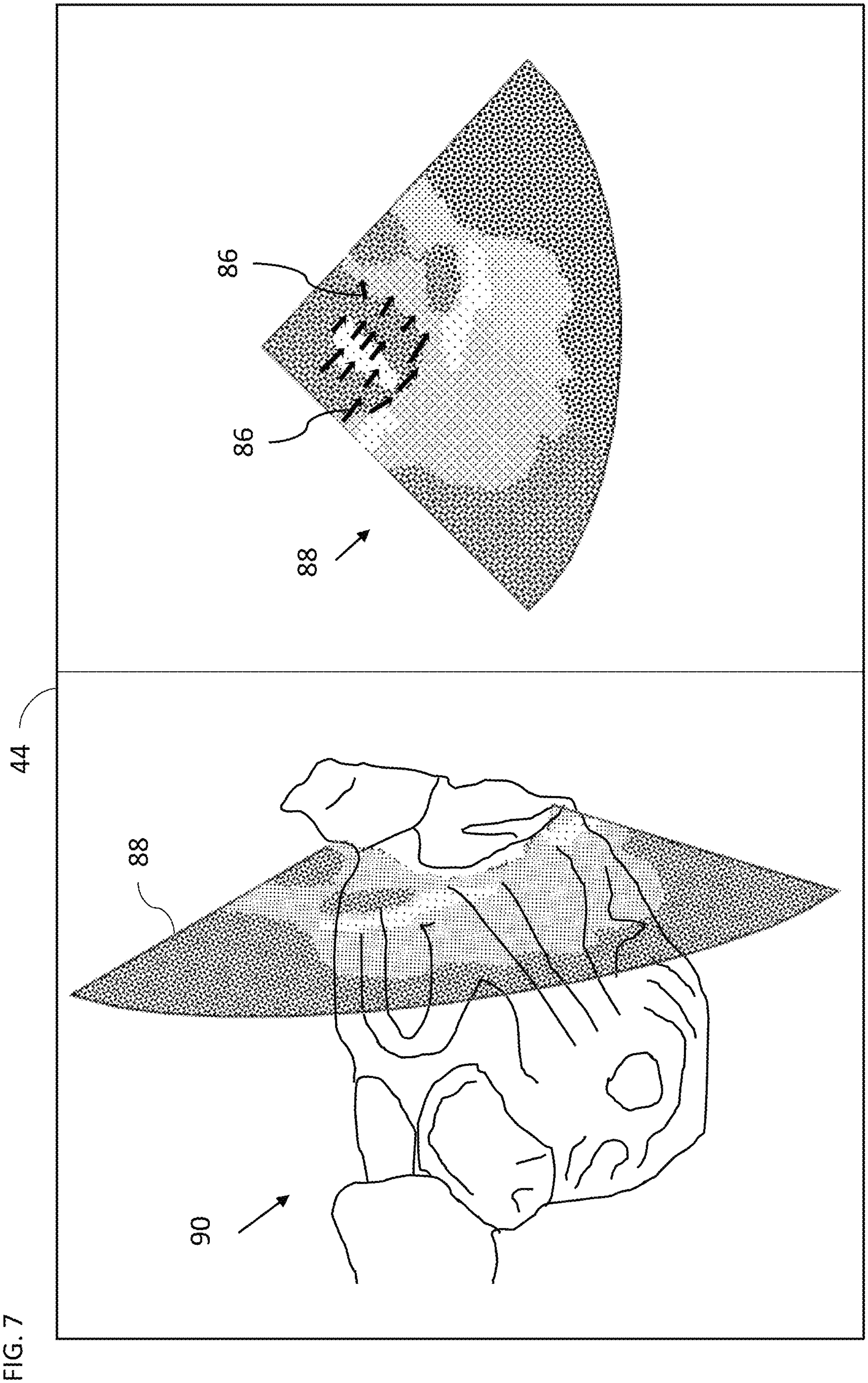
FIG. 7 is a schematic view of a 3D anatomical map and a 2D ultrasonic image with different representations of electro-anatomical data disposed thereon.

Reference is now made to FIG. 7, which is a schematic view of the 3D anatomical map 90 and a 2D ultrasonic image 88 with different representations 86 (only some labeled for the sake of simplicity) of electro-anatomical data disposed thereon. The respective representations 86 include respective multiple arrows. The respective multiple arrows represent velocity vectors or other propagation data.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 72% to 108%.

Examples

Example 1: A medical system, comprising: an ultrasound probe configured to captured ultrasonic images of at least part of a body part of a living subject; a display; and a processor configured to render to the display respective representations of respective electro-anatomical data subsets superimposed over respective ones of the ultrasonic images.

Example 2: The system according to example 1, wherein the respective representations include respective multi-colored lines or multi-colored regions.

Example 3: The system according to example 2, wherein the multi-colored lines or multi-colored regions represent local activation times or bipolar data.

Example 4: The system according to any of examples 1-3, wherein the respective representations include respective multiple arrows.

Example 5: The system according to example 4, wherein the respective multiple arrows represent velocity vectors.

Example 6: The system according to any of examples 1-5, wherein the respective electro-anatomical data subsets include any one or more of the following: local activation time data; bipolar data; propagation data; and velocity vectors.

Example 7: The system according to any of examples 1-6, wherein the processor is configured to render to the display one of the respective representations of one of the respective electro-anatomical data subsets superimposed over one of the ultrasonic images including an internal structure of a chamber of a heart with the one of the respective representations indicating electro-anatomical data of the internal structure.

Example 8: The system according to example 7, wherein the internal structure is a papillary muscle.

Example 9: The system according to example 7 or 8, wherein the electro-anatomical data of the internal structure includes bipolar data.

Example 10: The system according to any of examples 1-9, wherein the processor is configured to render to the display the respective representations of the respective electro-anatomical data subsets and a representation of a distal end of a catheter superimposed over the respective ones of the ultrasonic images.

Example 11: The system according to any of examples 1-10, wherein the processor is configured to find the respective electro-anatomical data subsets from an electro-anatomical dataset having electro-anatomical data positioned in three-dimension (3D) coordinate space within the respective ones of the ultrasonic images, or within a given threshold of, the respective ones of the ultrasonic images.

Example 12: The system according to example 11, further comprising: a mapping catheter configured to be inserted into the body part, and comprising at least one electrode configured to capture electrical activity from tissue of the body part at respective locations in the body part over time; and at least one position sensor configured to provide at least one signal indicative of positions of the ultrasound probe and the respective locations of the at least one electrode of the mapping catheter, wherein the processor is configured to: compute the respective locations of the at least one electrode and the positions of the ultrasound probe responsively to the at least one signal provided by the at least one position sensor; and compute the electro-anatomical data of the electro-anatomical dataset and corresponding positions of the electro-anatomical data in the 3D coordinate frame responsively to the captured electrical activity and the computed respective locations.

Example 13: The system according to example 12, wherein the at least one position sensor comprises: at least one first magnetic position sensor disposed on the mapping catheter; and at least one second magnetic position sensor disposed on the ultrasound probe.

Example 14: The system according to any of examples 11-13, wherein each respective ultrasound image of the respective ones of the ultrasonic images is a respective two-dimensional (2D) slice.

Example 15: The system according to any of examples 11-13, wherein each respective ultrasound image of the respective ones of the ultrasonic images is a respective three-dimensional (3D) image.

Example 16: A medical method, comprising: capturing ultrasonic images of at least part of a body part of a living subject; and rendering to a display respective representations of respective electro-anatomical data subsets superimposed over respective ones of the ultrasonic images.

Example 17: The method according to example 16, wherein the respective representations include respective multi-colored lines or multi-colored regions.

Example 18: The method according to example 17, wherein the multi-colored lines or multi-colored regions represent local activation times or bipolar data.

Example 19: The method according to example 16 or 17, wherein the respective representations include respective multiple arrows.

Example 20: The method according to example 19, wherein the respective multiple arrows represent velocity vectors.

Example 21: The system according to any of examples 16-20, wherein the respective electro-anatomical data subsets include any one or more of the following: local activation time data; bipolar data; propagation data; and velocity vectors.

Example 22: The method according to any of examples 16-21, wherein the rendering includes rendering to the display one of the respective representations of one of the respective electro-anatomical data subsets superimposed over one of the ultrasonic images including an internal structure of a chamber of a heart with the one of the respective representations indicating electro-anatomical data of the internal structure.

Example 23: The method according to any of examples 16-22, wherein the rendering includes rendering to the display the respective representations of the respective electro-anatomical data subsets and a representation of a distal end of a catheter superimposed over the respective ones of the ultrasonic images.

Example 24: The method according to any of examples 16-23, further comprising finding the respective electro-anatomical data subsets from an electro-anatomical dataset having electro-anatomical data positioned in three-dimension (3D) coordinate space within the respective ones of the ultrasonic images, or within a given threshold of, the respective ones of the ultrasonic images.

Various features of the disclosure which are, for clarity, described in the contexts of separate examples may also be provided in combination in a single example. Conversely, various features of the disclosure which are, for brevity, described in the context of a single example may also be provided separately or in any suitable sub-combination.

The examples described above are cited by way of example, and the present disclosure is not limited by what has been particularly shown and described hereinabove. Rather the scope of the disclosure includes both combinations and sub-combinations of the various features described hereinabove, as well as variations and modifications thereof which would occur to persons skilled in the art upon reading the foregoing description and which are not disclosed in the prior art.

What is claimed is:

1. A medical system, comprising:

a mapping catheter configured to be inserted into a body part of a living subject, the mapping catheter comprising at least one electrode configured to capture electrical activity from tissue of the body part at respective locations over time;

an ultrasound probe configured to capture ultrasonic images of at least a portion of the body part when inserted into the body of the living subject;

at least one position sensor configured to generate at least one signal indicative of positions of the ultrasound probe and of the at least one electrode of the mapping catheter;

a display; and a processor configured to:

determine, in real time, positions of the ultrasound probe and of the at least one electrode of the mapping catheter within a shared three-dimensional (3D) coordinate frame responsive to the at least one signal generated by the at least one position sensor;

determine electro-anatomical data from the electrical activity captured by the at least one electrode of the mapping catheter, and corresponding positions of the electro-anatomical data in the shared 3D coordinate frame;

determine, from an electro-anatomical dataset comprising the electro-anatomical data, electro-anatomical data positioned within, or within a threshold of, a respective one of two-dimensional (2D) ultrasonic images in the shared 3D coordinate frame;

render to the display respective representations of respective electro-anatomical data subsets superimposed on corresponding ones of the 2D ultrasonic images captured by the ultrasound probe;

dynamically update, in real time, the superimposed representations in response to movement of the ultrasound probe, wherein the respective electro-anatomical data subsets change to reflect new positions of the corresponding ones of the 2D ultrasonic images in the shared 3D coordinate frame; and display, in the superimposed representations, color-encoded lines or regions corresponding to local activation time (LAT) data or bipolar data.

2. The system according to claim 1, wherein the respective representations include respective multiple arrows.

3. The system according to claim 2, wherein the respective multiple arrows represent velocity vectors.

4. The system according to claim 1, wherein the processor is configured to render to the display a respective representation of one of the electro-anatomical data subsets superimposed over one of the 2D ultrasonic images including an internal structure of a chamber of a heart, with the respective representation indicating electro-anatomical data of the internal structure.

5. The system according to claim 4, wherein the internal structure is a papillary muscle.

6. The system according to claim 5, wherein the electro-anatomical data of the internal structure includes bipolar data.

7. The system according to claim 1, wherein the processor is configured to render to the display the respective representations of the electro-anatomical data subsets and a representation of a distal end of a catheter superimposed over the respective ones of the ultrasonic images.

8. The system according to claim 1, wherein the at least one position sensor comprises: at least one first magnetic position sensor disposed on the mapping catheter; and at least one second magnetic position sensor disposed on the ultrasound probe.

9. The system according to claim 1, wherein each respective ultrasound image of the respective ones of the ultrasonic images is a respective two-dimensional (2D) fan image in a beam plane of the ultrasound probe.

10. The system according to claim 1, wherein each respective ultrasound image of the respective ones of the ultrasonic images is a respective three-dimensional (3D) image.

11. A medical method, comprising:

capturing electrical activity from tissue of a body part of a living subject at respective locations over time using at least one electrode of a mapping catheter;

capturing two-dimensional (2D) ultrasonic images of at least a portion of the body part of the living subject using an ultrasound probe;

determining, in real time, positions of the ultrasound probe and of the at least one electrode of the mapping catheter within a shared three-dimensional (3D) coordinate frame responsive to at least one signal generated by at least one position sensor;

determining electro-anatomical data from the electrical activity captured by the at least one electrode of the mapping catheter, and corresponding positions of the electro-anatomical data in the shared 3D coordinate frame;

determining, from an electro-anatomical dataset comprising the electro-anatomical data, respective electro-anatomical data subsets comprising electro-anatomical data positioned within, or within a threshold of, respective ones of the 2D ultrasonic images in the shared 3D coordinate frame;

rendering to a display respective representations of the respective electro-anatomical data subsets superimposed on corresponding ones of the 2D ultrasonic images captured by the ultrasound probe;

wherein the respective representations include respective color-encoded lines or regions corresponding to local activation time (LAT) data or bipolar data; and wherein the respective representations superimposed over the 2D ultrasonic images are dynamically updated, in real time, in response to movement of the ultrasound probe within the body part, wherein the respective electro-anatomical data subsets change to reflect new positions of the corresponding ones of the 2D ultrasonic images in the shared 3D coordinate frame.

12. The method according to claim 11, wherein the respective representations include respective multiple arrows.

13. The method according to claim 12, wherein the respective multiple arrows represent velocity vectors.

14. The method according to claim 11, wherein the electro-anatomical data subsets include any one or more of the following: local activation time data; bipolar data; propagation data; and velocity vectors.

15. The method according to claim 11, wherein the rendering includes rendering to the display one of the respective representations of one of the electro-anatomical data subsets superimposed over one of the ultrasonic images including an internal structure of a chamber of a heart with the one of the respective representations indicating electro-anatomical data of the internal structure.

16. The method according to claim 11, wherein the rendering includes rendering to the display the respective representations of the respective electro-anatomical data subsets and a representation of a distal end of a catheter superimposed over the respective ones of the ultrasonic images.

17. The method according to claim 11, further comprising finding the electro-anatomical data subsets from an electro-anatomical dataset having electro-anatomical data positioned in three-dimension (3D) coordinate space within the respective ones of the ultrasonic images, or within a given threshold of, the respective ones of the ultrasonic images.

* * * * *